(12) United States Patent
Sage

(10) Patent No.: US 9,037,243 B2
(45) Date of Patent: May 19, 2015

(54) LOW INSERTION FORCE ELECTRICAL CONNECTOR FOR IMPLANTABLE MEDICAL DEVICES

(71) Applicant: Greatbatch Ltd., Clarence, NY (US)

(72) Inventor: Shahn S. Sage, Andover, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/514,817

(22) Filed: Oct. 15, 2014

(65) Prior Publication Data
US 2015/0032193 A1 Jan. 29, 2015

Related U.S. Application Data

(63) Continuation of application No. 13/868,509, filed on Apr. 23, 2013, now Pat. No. 8,934,974, which is a continuation of application No. 13/045,779, filed on Mar. 11, 2011, now Pat. No. 8,428,724.

(51) Int. Cl.
| | |
|---|---|
| *A61N 1/375* | (2006.01) |
| *H01R 13/187* | (2006.01) |
| *A61N 1/05* | (2006.01) |
| *H01R 13/33* | (2006.01) |
| *A61N 1/36* | (2006.01) |
| *H01R 24/58* | (2011.01) |
| *H01R 107/00* | (2006.01) |

(52) U.S. Cl.
CPC .......... *A61N 1/3752* (2013.01); *Y10T 29/49117* (2015.01); *A61N 1/36125* (2013.01); *H01R 13/187* (2013.01); *H01R 24/58* (2013.01); *H01R 2107/00* (2013.01); *H01R 2201/12* (2013.01); *A61N 1/0551* (2013.01); *H01R 13/33* (2013.01); *Y10S 439/909* (2013.01); *A61N 1/3605* (2013.01)

(58) Field of Classification Search
None
See application file for complete search history.

(56) References Cited

U.S. PATENT DOCUMENTS

| | | | |
|---|---|---|---|
| 4,112,953 | A | 9/1978 | Shanker et al. |
| 4,655,462 | A | 4/1987 | Balsells |
| 4,655,945 | A | 4/1987 | Balsells |
| 4,678,210 | A | 7/1987 | Balsells |
| 4,804,290 | A | 2/1989 | Balsells |
| 4,805,943 | A | 2/1989 | Balsells |

(Continued)

FOREIGN PATENT DOCUMENTS

WO 2011017432 2/2011

OTHER PUBLICATIONS

International, "PTO02386EP", 12158574.9-2305, Sep. 10, 2012.

*Primary Examiner* — Kennedy Schaetzle
(74) *Attorney, Agent, or Firm* — Michael P. Horvath

(57) ABSTRACT

A low-insertion force electrical connector for implantable medical devices includes a housing with a pair of opposing sidewalls each with center openings oriented generally concentrically around a center axis. An inner coil is located in a recess with a coil axis generally co-linear with the center axis of the center openings. The inner coil includes an outer diameter less than a recess diameter, and an inner diameter greater than a center opening diameter. An outer coil is threaded onto the inner coil. The outer coil has an outer diameter less than the recess diameter, and an inner diameter less than the center opening diameter. The outer coil is radially expanded within the recess in response to engagement with contact rings on the implantable medical device, such that the outer diameter of the outer coil is at least equal to the recess diameter.

20 Claims, 15 Drawing Sheets

(56) References Cited

U.S. PATENT DOCUMENTS

| | | | | |
|---|---|---|---|---|
| 4,826,144 | A | 5/1989 | Balsells | |
| 4,830,344 | A | 5/1989 | Balsells | |
| 4,876,781 | A | 10/1989 | Balsells | |
| 4,890,937 | A | 1/1990 | Balsells | |
| 4,893,795 | A | 1/1990 | Balsells | |
| 4,906,109 | A | 3/1990 | Balsells | |
| 4,907,788 | A | 3/1990 | Balsells | |
| 4,915,366 | A | 4/1990 | Balsells | |
| 4,934,666 | A | 6/1990 | Balsells | |
| 4,942,876 | A * | 7/1990 | Gotthardt | 607/37 |
| 4,961,253 | A | 10/1990 | Balsells | |
| 4,964,204 | A | 10/1990 | Balsells | |
| 4,966,564 | A * | 10/1990 | Foote | 439/840 |
| 4,974,821 | A | 12/1990 | Balsells | |
| 5,069,209 | A | 12/1991 | Posin | |
| 5,072,070 | A | 12/1991 | Balsells | |
| 5,079,388 | A | 1/1992 | Balsells | |
| 5,082,390 | A | 1/1992 | Balsells | |
| 5,091,606 | A | 2/1992 | Balsells | |
| 5,108,078 | A | 4/1992 | Balsells | |
| 5,117,066 | A | 5/1992 | Balsells | |
| 5,134,244 | A | 7/1992 | Balsells | |
| 5,139,243 | A | 8/1992 | Balsells | |
| 5,139,276 | A | 8/1992 | Balsells | |
| 5,160,122 | A | 11/1992 | Balsells | |
| 5,161,806 | A | 11/1992 | Balsells | |
| 5,203,849 | A | 4/1993 | Balsells | |
| 5,239,737 | A | 8/1993 | Balsells | |
| 5,265,890 | A | 11/1993 | Balsells | |
| 5,358,224 | A | 10/1994 | Balsells | |
| 5,411,348 | A | 5/1995 | Balsells | |
| 5,474,309 | A | 12/1995 | Balsells et al. | |
| 5,503,375 | A | 4/1996 | Balsells et al. | |
| 5,545,842 | A | 8/1996 | Balsells | |
| 5,575,487 | A | 11/1996 | Balsells | |
| 5,599,027 | A | 2/1997 | Balsells et al. | |
| 5,615,870 | A | 4/1997 | Balsells et al. | |
| 5,709,371 | A | 1/1998 | Balsells | |
| 5,730,628 | A | 3/1998 | Hawkins | |
| 5,791,638 | A | 8/1998 | Balsells | |
| 5,979,904 | A | 11/1999 | Balsells | |
| 5,984,316 | A | 11/1999 | Balsells | |
| 5,992,856 | A | 11/1999 | Balsells et al. | |
| 6,050,572 | A | 4/2000 | Balsells et al. | |
| 6,161,838 | A | 12/2000 | Balsells | |
| 6,192,279 | B1 | 2/2001 | Barreras et al. | |
| 6,264,205 | B1 | 7/2001 | Balsells | |
| 6,641,141 | B2 | 11/2003 | Schroeder | |
| 6,749,358 | B2 | 6/2004 | Balsells | |
| 6,835,084 | B2 | 12/2004 | Poon et al. | |
| 6,895,276 | B2 | 5/2005 | Kast et al. | |
| 6,958,616 | B1 | 10/2005 | Mahoney et al. | |
| 7,003,351 | B2 * | 2/2006 | Tvaska et al. | 607/37 |
| 7,047,077 | B2 | 5/2006 | Hansen et al. | |
| 7,055,812 | B2 | 6/2006 | Balsells | |
| 7,070,455 | B2 | 7/2006 | Balsells | |
| 7,110,827 | B2 | 9/2006 | Sage et al. | |
| 7,174,964 | B2 | 2/2007 | Cook et al. | |
| 7,175,441 | B2 | 2/2007 | Naviaux et al. | |
| 7,195,523 | B2 | 3/2007 | Naviaux | |
| 7,210,398 | B2 | 5/2007 | Balsells | |
| 7,286,882 | B2 | 10/2007 | Cole | |
| 7,299,095 | B1 | 11/2007 | Barlow et al. | |
| 7,316,593 | B2 | 1/2008 | Balsells | |
| 7,464,750 | B2 | 12/2008 | Schapel et al. | |
| 7,538,289 | B2 | 5/2009 | Carroll | |
| 7,722,415 | B2 | 5/2010 | Chansrivong | |
| 7,769,459 | B2 | 8/2010 | Balsells | |
| 7,822,477 | B2 | 10/2010 | Rey et al. | |
| 7,838,787 | B2 | 11/2010 | Balsells et al. | |
| 7,858,892 | B2 | 12/2010 | Balsells et al. | |
| 8,046,074 | B2 | 10/2011 | Barker | |
| 8,428,724 | B2 | 4/2013 | Sage | |
| 2003/0163171 | A1 | 8/2003 | Kast et al. | |
| 2004/0034393 | A1 | 2/2004 | Hansen et al. | |
| 2004/0167582 | A1 | 8/2004 | Tvaska et al. | |
| 2004/0215303 | A1 | 10/2004 | Sage | |
| 2006/0004419 | A1 * | 1/2006 | Olbertz | 607/37 |
| 2008/0246231 | A1 | 10/2008 | Sjostedt et al. | |
| 2009/0197476 | A1 | 8/2009 | Wallace | |
| 2011/0059639 | A1 | 3/2011 | Dilmaghanian et al. | |
| 2011/0264162 | A1 | 10/2011 | Osypka et al. | |
| 2011/0270363 | A1 | 11/2011 | Schramm et al. | |
| 2012/0053663 | A1 | 3/2012 | Rodby et al. | |

* cited by examiner

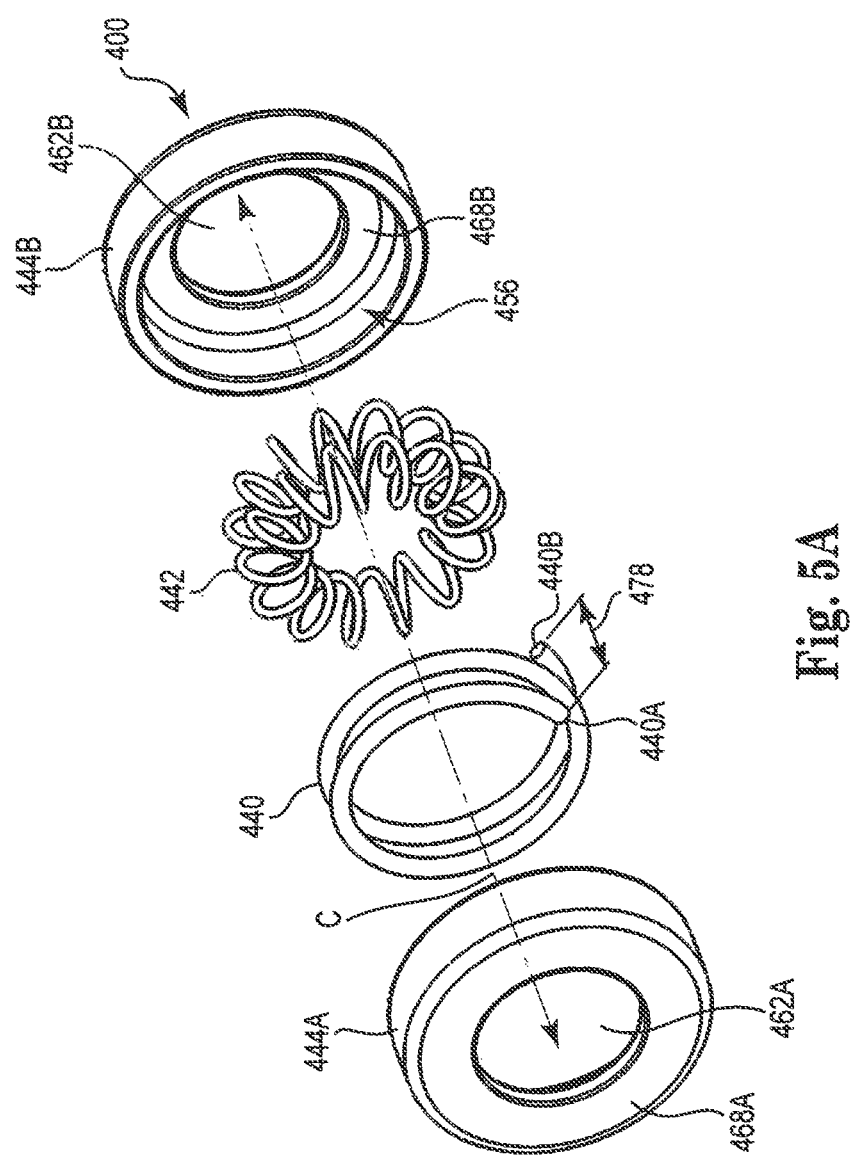

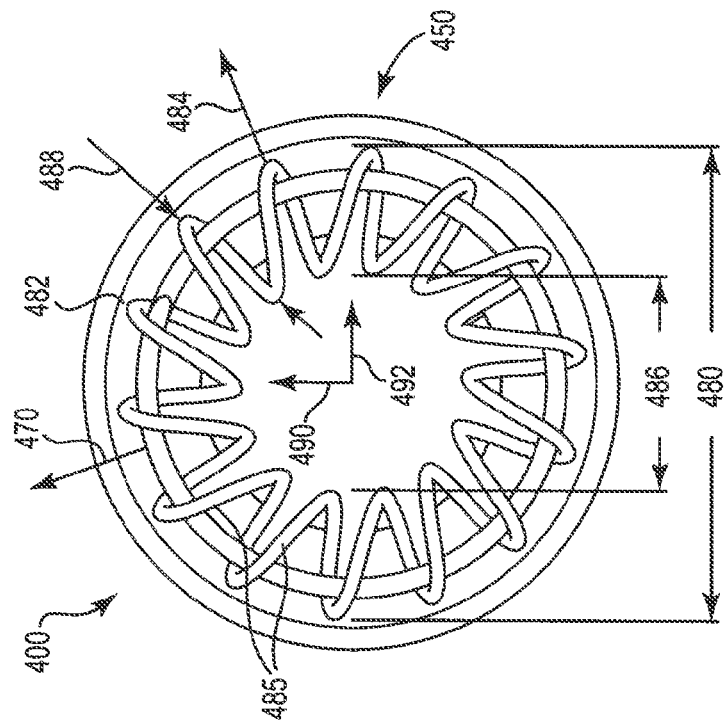
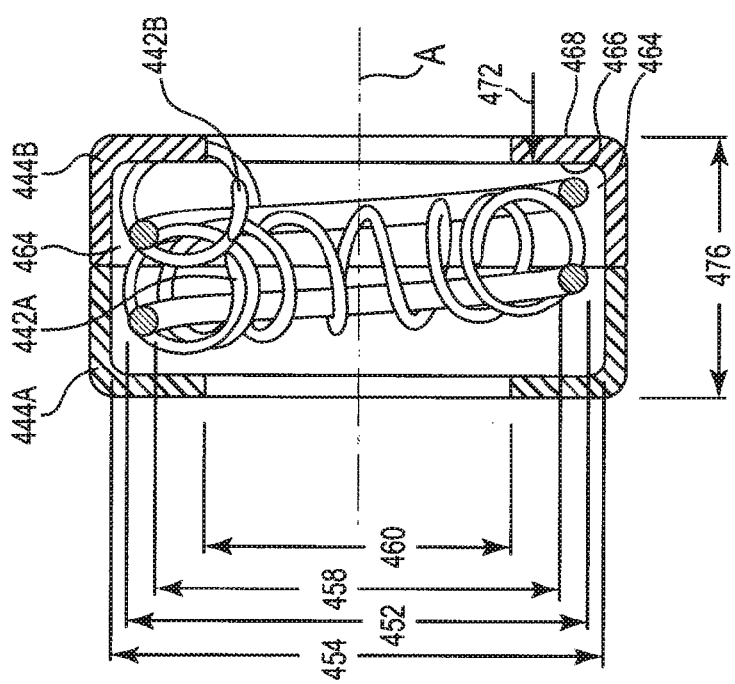
Fig. 5C
Fig. 5B

LOW INSERTION FORCE ELECTRICAL CONNECTOR FOR IMPLANTABLE MEDICAL DEVICES

CLAIM OF PRIORITY

This application is a continuation of and claims the benefit of priority under 35 U.S.C. §120 to Sage, U.S. patent application Ser. No. 13/868,509, entitled "LOW INSERTION FORCE ELECTRICAL CONNECTOR FOR IMPLANTABLE MEDICAL DEVICES", filed on Apr. 23, 2013, which is a continuation of and claims the benefit of priority to Sage, U.S. patent application Ser. No. 13/045,779, entitled "LOW INSERTION FORCE ELECTRICAL CONNECTOR FOR IMPLANTABLE MEDICAL DEVICES", filed on Mar. 11, 2011, which are each incorporated by reference herein in its entirety.

FIELD

The present disclosure is directed to a low-insertion force electrical connector for implantable medical devices, and to a connector assembly including a plurality of the low-insertion force electrical contacts.

BACKGROUND

Implantable medical electronics devices consist of an implanted pulse generator that is used to provide electrical stimulation to certain tissues and an implantable lead or leads that are used to transmit the electrical impulse to the targeted tissues. Examples include cardiac pacemaking, and a number of related applications for cardiac rhythm management, treatments for congestive heart failure, and implanted defibrillators. Other applications for implantable pulse generators include neurostimulation with a wide range of uses such as pain control, nervous tremor mitigation, incontinent treatment, epilepsy seizure reduction, vagus nerve stimulation for clinical depression, and the like. This rapidly growing field will undoubtedly have even wider application in the future.

These implantable medical devices generally include an implanted pulse generator that generates electrical pulses or signals that are transmitted to a targeted tissue or tissues through an electrode on an implanted lead. Once the leads are implanted in the body, removal may involve major surgery with attendant risk factors. Therefore, a reliable method of connecting and disconnecting the leads from the implantable pulse generator is required in order to service or replace the implanted pulse generator.

Pulse generators are typically hermetically sealed housing containing circuitry and a power supply. Current practice is to place a molded header containing a connector on the housing to provide a structure to electrically couple with contact rings on the lead with the circuitry, such as illustrated in U.S. Pat. Publication No. 2003/0163171 (Kast et al.). While some pulse generators only require a few leads, pulse generators for some applications are very complex and require a large number of discrete electrical impulses each delivered by a discrete lead. In these more complex applications, each electrical impulse requires a discrete conductive path between the impulse generator and the lead electrode.

The proximal ends of the leads generally includes a series of conductive rings separated by insulating spacers so that when it is fully inserted into the connector assembly, each contact ring is placed in contact with a discrete contact. Each contact in turn is electrically coupled to a discrete lead on the circuitry for the implantable pulse generator.

The proximal ends of the leads serve as a male portion adapted to be received within a corresponding female connector on the implantable pulse generator housing. One such female electrical connector includes a cylindrical outer housing having a transverse circumferential groove or channel within the interior face of the housing. A metallic coil spring is disposed within the circumferential channel, providing electrical continuity between the spring and the outer metallic housing. Electrical connectors of this type are available from Bal Seal Engineering Company, Inc., Foothill, Calif. USA.

The male end bearing the conductive rings is preferably dimensioned to be insertable into the female portion with minimum force. The springs in the individual contacts provide a radially inward directed force on the contact rings to establish the electrical contact.

U.S. Pat. No. 4,655,462 (Balsells) discloses a coiled spring with a plurality of coils disposed in a preselected acute angle (i.e., pre-canted) with the centerline of the coil spring. The coil spring exerts a constant force in a loading direction approximately normal to the centerline of the coiled spring in response to a deflection of the coil spring along the loading direction. Pre-canted refers to each coil having a back portion disposed at a back angle with respect to the centerline and the forward portion disposed at a front angle with respect to the centerline, where the front angle being greater than the back angle before the coil spring is formed in a toroidal-shape.

U.S. Pat. No. 7,316,593 (Balsells) and U.S. Pat. No. 7,195,523 (Naviaux) disclose a connector assembly that uses a pre-canted spring to provide a fairly linear force-deflection curve during insertion of the contact end of the lead. The pre-canted spring also compensates for any irregularities on the surface of the contact rings on the lead. The pre-canted springs are typically retained in grooved housing or an annular ring that limits radial expansion, requiring very tight tolerances between the contact rings on the lead and the springs.

U.S. Pat. No. 7,110,827 (Sage) is directed to an electrical connector for medical leads having a solderless wiring connection to the circuitry in the implantable pulse generator. The housing includes at least one hole adjacent a mechanically deformable side wall for mechanically securing an electrical conductor inserted within the hole.

U.S. Pat. No. 7,299,095 (Barlow et al.) is directed to an electrical contact assembly including an annular housing defining an interior space. The housing includes a tubular wall having an outer surface facing the interior space, and an inner surface defining a central opening adapted to receive an electrical contact. Contained within the interior space of the housing is a garter spring encircling the outer surface of the wall under preload so that a portion of the inner diameter of the spring projects through the aperture into the central opening of the housing for engaging an electrical contact received within the central opening.

BRIEF SUMMARY

The present disclosure is directed to a low-insertion force electrical connector for implantable medical devices and a connector assembly including a plurality of the electrical contacts.

The present electrical connector permits the coil contacts to move in multiple degrees of freedom, without pre-canting the coil spring, permitting wider tolerances between the electrical contact and the proximal end of the therapy delivery element or extension thereof. In particular, pre-canted springs are simply canted further when a radially outward force is applied. The coil springs of the present disclosure can also be radially compressed in response to a radially outward force, not simply canted further. Consequently, the radial compression of the present coil springs is an additional degree of freedom for the spring assembly not present in the pre-canted coil springs of the prior art.

In one embodiment, the electrical contacts include a housing with a pair of opposing sidewalls each with center openings oriented generally concentrically around a center axis, and a recess with a recess diameter. An inner coil is located in the recess with a coil axis generally parallel with the center axis of the center openings. The inner coil includes an outer diameter less than the recess diameter, and an inner diameter greater than a center opening diameter. An outer coil is arranged in a generally toroidal-shape and threaded onto the inner coil. The outer coil has an outer diameter less than the recess diameter, and an inner diameter less than the center opening diameter. The outer coil is radially expanded within the recess in response to engagement with contact rings on the implantable medical device, such that the outer diameter of the outer coil is at least equal to the recess diameter.

In one embodiment, the outer coil is displaced within the recess relative to the center opening in response to engagement with the contact rings on the implantable medical device. In another embodiment, individual coils of the outer coil are radially compressed against the housing in response to engagement with the contact rings on the implantable medical device. The outer coil is preferably displaced relative to the center opening in at least three degrees of freedom in response to engagement with the contact rings on the implantable medical device. In particular, the outer coil is adapted to be (i) displaced radially within the recess relative to the center openings, (ii) displaced linearly within the recess relative to the center openings, and (iii) individual coils of the outer coil are radially compressed or deformed relative to the center openings.

The housing can be a conductive material or a nonconductive material.

The present disclosure is also directed to a connector assembly including a plurality of the electrical contacts oriented with co-linear center axes. The plurality of electrical contacts forms a conductor path for receiving proximal end of an implantable therapy delivery element or an extension for a therapy delivery element. In one embodiment, a dielectric material separates each of the electrical contacts, without blocking the conductor path. A housing maintains the position of the discrete electrical contacts and the dielectric material relative to the conductor path.

The present disclosure is also directed to an implantable pulse generator retained in a housing. A connector assembly with a plurality of the electrical contacts oriented with co-linear center axes is attached to the housing. A plurality of conductive members electrically couples the inner and outer coils to the circuitry of the pulse generator.

The present disclosure is also directed to a method of electrically coupling an implantable medical device with an electrical pulse generator to an implantable therapy delivery element. The method includes arranging center openings on each of a plurality of electrical contacts to form a conductive path of a connector assembly. Each of the electrical contacts includes a housing with a recess and a recess diameter. An inner coil is located in the recess with a coil axis generally parallel with a center axis of the center openings. The inner coil includes an outer diameter less than the recess diameter, and an inner diameter greater than a center opening diameter. An outer coil is arranged in a generally toroidal-shape and is threaded onto the inner coil. The outer coil has an outer diameter less than the recess diameter, and an inner diameter less than the center opening diameter. The housings are electrically coupled with circuitry in the implantable pulse generator. A proximal end of the implantable therapy delivery element is inserted along the conductive path to electrically couple the contact rings with the outer coils in the connector assembly. The outer coils are radially expanded within the recesses in response to engagement with the contact rings on the implantable medical device, such that the outer diameters of the outer coils are at least equal to the recess diameter.

One embodiment includes a method of displacing the outer coil within the recess relative to the center opening in response to engagement with the contact rings on the implantable medical device. Another embodiment includes a method of radially compressing individual coils of the outer coil against the housing in response to engagement with the contact rings on the implantable medical device. The method preferably includes displacing the outer coil relative to the center opening in at least three degrees of freedom in response to engagement with the contact rings on the implantable medical device.

BRIEF DESCRIPTION OF THE SEVERAL VIEWS OF THE DRAWING

FIG. 5A is an exploded view of an electrical connector for a medical device in accordance with an embodiment of the present disclosure.

FIG. 5B is a side sectional view of the electrical connector of FIG. 5A.

FIG. 5C is a front sectional view of the electrical connector of FIG. 5A.

DETAILED DESCRIPTION OF SOME EMBODIMENTS

The description that follows relates to a spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, extensions for any of the above, or combinations thereof. "Target tissue site" refers generally to the target site for implantation of a therapy delivery element, regardless of the type of therapy.

Figure 1:
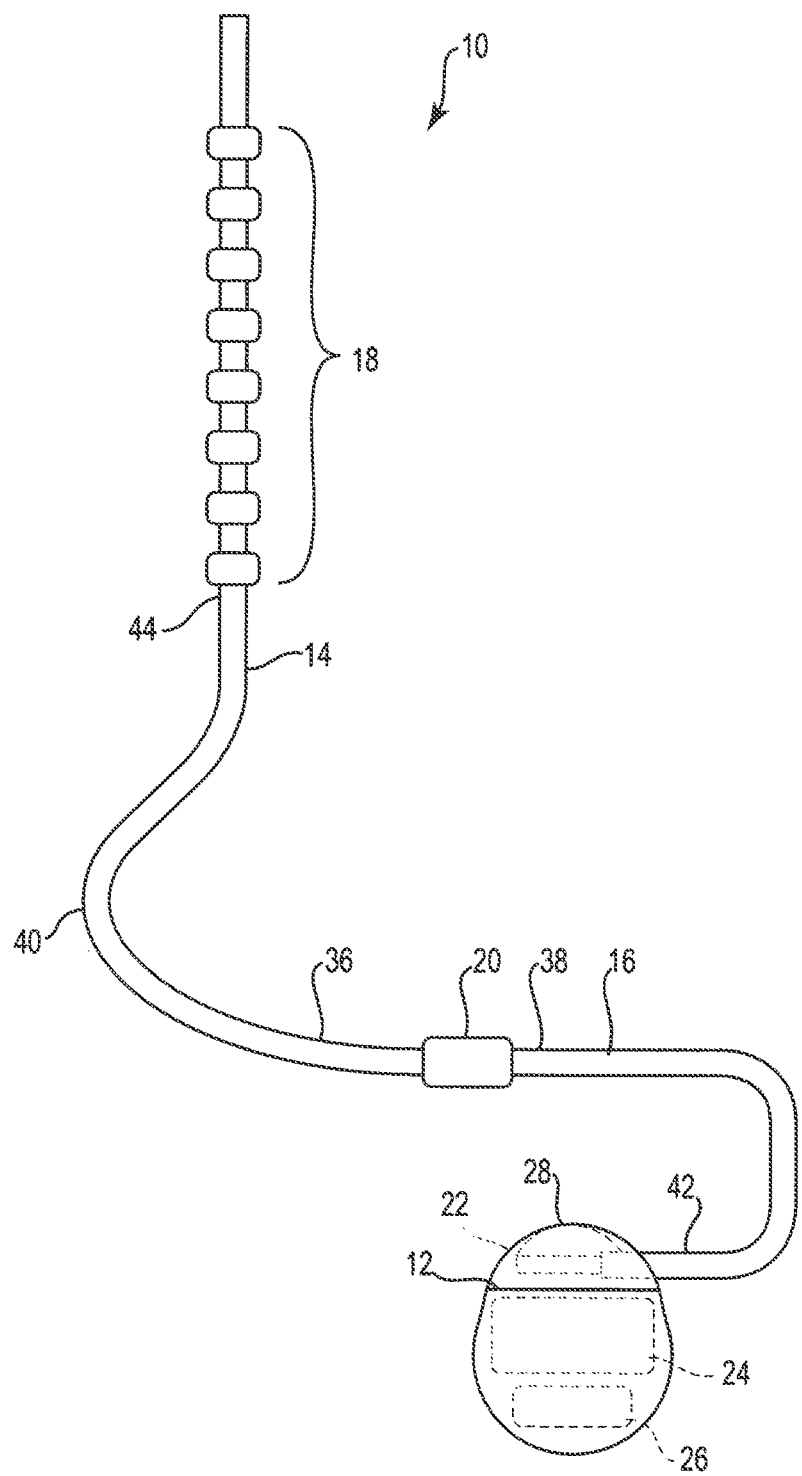
FIG. 1 is a schematic illustration of a therapy delivery system.

FIG. 1 illustrates a generalized therapy delivery system 10 that may be used in spinal cord stimulation (SCS), as well as other stimulation applications. The therapy delivery system 10 generally includes an implantable pulse generator 12, an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10 (See e.g., FIG. 3).

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be extruded from as a uni-body construction.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector assembly 22 associated with housing 28. Alternatively, the proximal end 36 of the therapy delivery element 14 can be electrically coupled directly to the connector 20.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 is protected from the body tissue and fluids. The connector assembly 22 is disposed in a portion of the housing 28 that is, at least initially, not sealed. The connector assembly 22 carries a plurality of contacts that electrically couple with respective terminals at proximal ends of the therapy delivery element 14 or extension lead 16. Electrical conductors extend from the connector assembly 22 and connect to the electronic subassembly 24.

Figure 2:
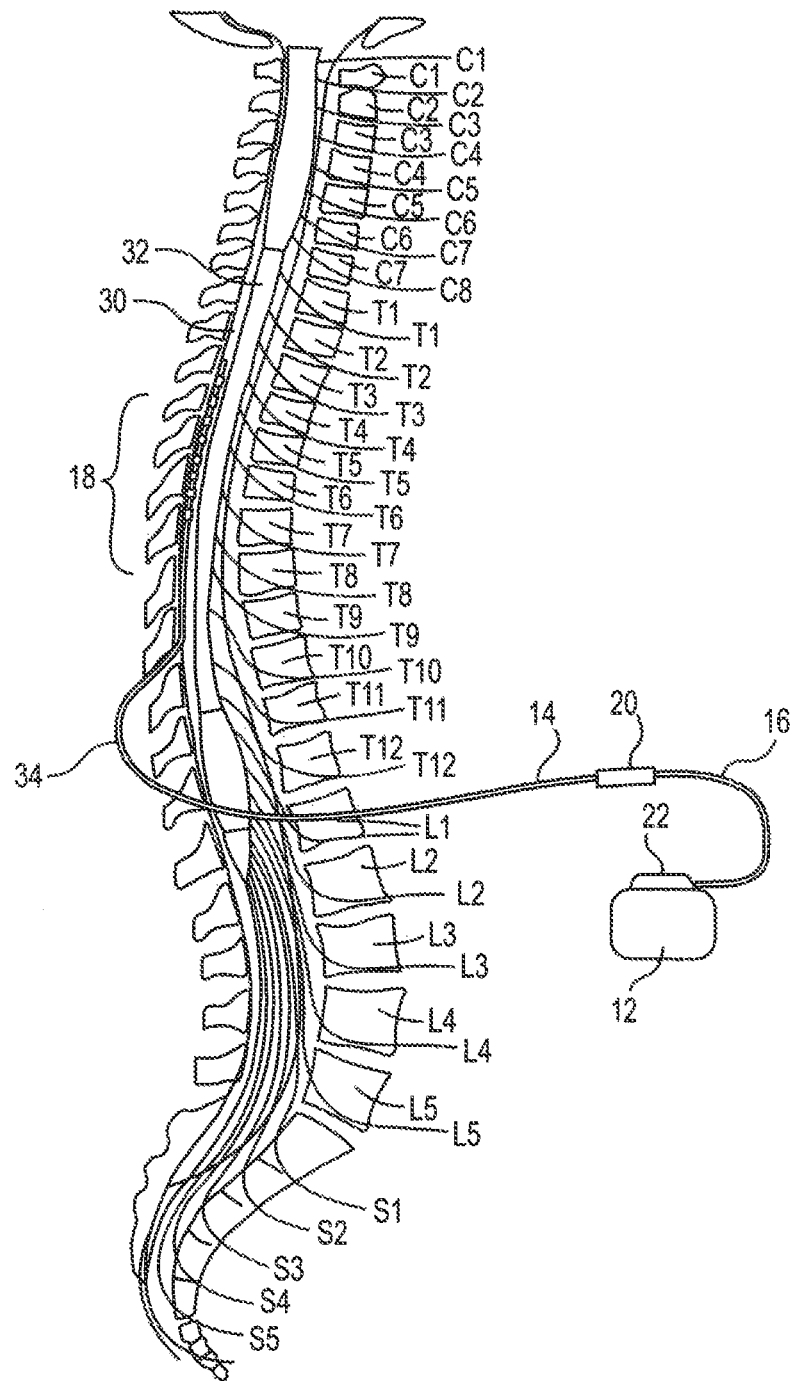
FIG. 2 is a schematic illustration of an environment for a therapy delivery system in accordance with an embodiment of the present disclosure.

FIG. 2 illustrates the therapy delivery element 14 implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 3:
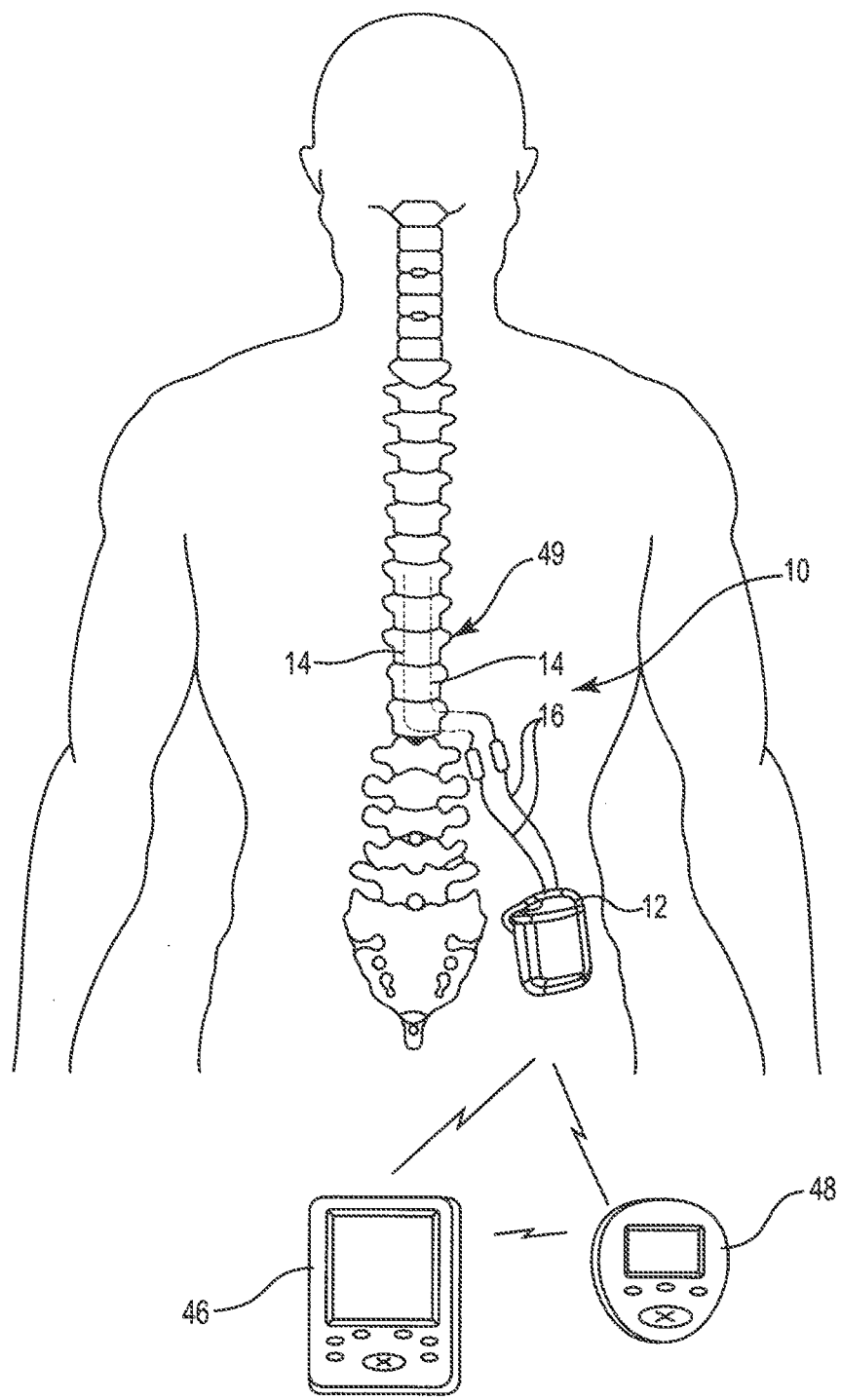
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector assembly 22 of the implantable pulse generator 12, since different manufacturers use different connectors at the ends of their stimulation leads and are not always compatible with the connector assembly 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. En this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 48, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 12 is located remotely from target location 49 for therapy, the therapy delivery element 14 and/or the extension leads 16 is typically routed through a pathways subcutaneously formed along the torso of the patient to a subcutaneous pocket where the implantable pulse generator 12 is located.

Figure 4A:
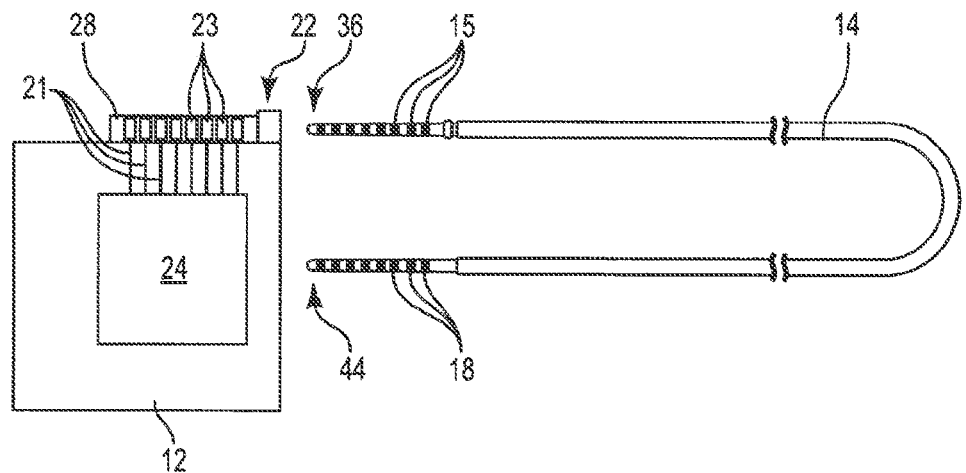
FIG. 4A is a schematic illustration of an implantable pulse generator with a connector assembly in accordance with an embodiment of the present disclosure.

FIG. 4A illustrates the therapy delivery element 14 including one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22.

The connector assembly 22 includes a plurality of discrete contacts 23 located in the housing 28 that electrically couple contact rings 15 on the proximal end of the therapy delivery element 14. The discrete contacts 23 are electrically coupled to circuitry 24 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can independently deliver electrical impulses to each of the electrodes 18.

Figure 4B:
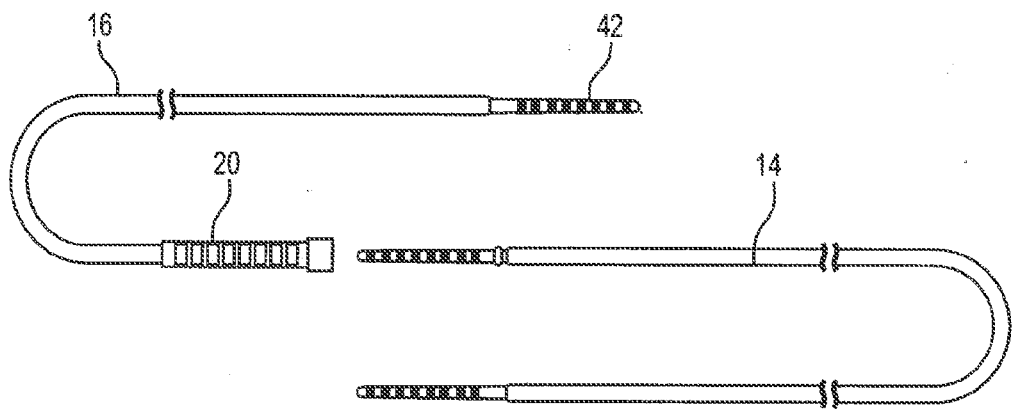
FIG. 4B is a schematic illustration of a lead extension with a connector assembly in accordance with an embodiment of the present disclosure.

Alternatively, the therapy delivery element 14 can be coupled to the implantable pulse generator 12 through one or more lead extensions 16, as illustrated in FIG. 4B. The connector 20 at the distal end 38 of the lead extension 16 preferably includes a plurality of the contacts 23 configured in a manner similar to the connector assembly 22.

FIG. 5A is an exploded view of an individual contact 400, such as the contact 23, used in the implantable pulse generator 12 and/or the lead extension 16, in accordance with an embodiment of the present disclosure. Inner coil 440 and outer coil 442 are retained in housing 444A, 444B (collectively "444"). In the illustrated embodiment, housing 444 is a two-part assembly made from a conductive material. Alternatively, the housing 444 can be a single component and may be made from a dielectric material, as discussed below.

As best illustrated in FIGS. 5B and 5C, the housing 444 includes a pair of annular sidewalls 468A, 468B ("468") with center openings 462A, 462B ("462") that form recess 456 with depth 476. In the illustrated embodiment, the recess 456 has the shape of an open cylinder. While the illustrated embodiment shows the recess 456 with a rectangle cross-section, the recess 456 can have a variety of other cross-sectional shapes, including for example, circular or elliptical. The center openings 462A, 462B have preferably the same diameter 460 and are located concentrically around center axis A. The axis A also defines a conductor path along which the proximal ends 36 or 42 of the therapy delivery element 14 or extension 16 is inserted.

The inner coil 440 has a coil axis C (see FIG. 5A) generally co-linear with the axis A. Inner coil 440 preferably has an outer diameter 452 less than inner diameter 454 of recess 456 in housing 444, but an inner diameter 458 that is greater than diameter 460 of center openings 462. Consequently, proximal ends 36, 42 typically do not directly contact inner coil 440 during insertion into connector assembly 22.

Gap 464 between the outer diameter 452 of the inner coil 440 and the inner diameter 454 of the recess 456 permits the inner coil 440 to be displaced within the recess 456, either by shifting with the recess 456 or expanding in radial direction 470 by elastic deformation of the inner coil 440. Inner surfaces 466 of annular sidewalls 468 of the housing 444, however, preferably engage with the inner coil 440 to restrict axial movement within the recess 456, except due to elastic deformation. In one embodiment, the depth 476 is less than the height 478 (see FIG. 5A) of inner coil 440 so the annular sidewalls 468 apply a compressive force 472 to inner coil 440.

The inner coils 440 are typically helical in shape, but other regular and irregular shapes are possible. The inner coil 440 preferably has a rotation of greater than 360 degrees, or more than one full turn.

The inner coil 440 is preferably threaded into outer coil 442 to form a coil assembly 450. The inner coil 440 retains the outer coil 442 in a generally toroidal-shape. In embodiments where the outer coil 442 extends along the inner coil 440 for more than 360 degrees, the coil ends 442A, 442B overlap.

The outer coil 442 includes a plurality of individual coils 485 that are not pre-canted prior to being formed in the toroidal shape. The term "pre-canted" as used in reference to a coil spring means that each coil has a back portion disposed at a back angle with respect to a centerline of the coil and a forward portion disposed at a front angle with respect to the centerline, where the front angle is greater than the back angle, before the coil spring is formed in a toroidal-shape. FIG. 4a of U.S. Pat. No. 4,655,462 (Balsells), which is hereby incorporated by reference, discloses an example of a pre-canted coil spring. The present disclosure preferably does not use pre-canted coil springs for the outer coils.

In a preferred embodiment, distal ends 440A, 440B of the inner coil 440 (see FIG. 5A) preferably contact inner surfaces 466 of the housing 444, thereby capturing the outer coil 442. Consequently, distal ends 442A, 442B of the outer coil 442 do not need to be welded or otherwise attached. The distal ends 442A, 442B also preferably overlap, to further secure the outer coil 442 to the inner coil 440.

Outer coil 442 also preferably has an outer diameter 480 that is less than inner diameter 454 of the recess 456. The inner diameter 486 of the outer coil 442, however, is preferably less than the diameter 460 of the center opening 462. The outer coil 442 preferably extends into the center opening 462 an amount greater than the gap 482, so that the outer coil 442 compressively engages with the contact rings 15 on the proximal end 36 when the therapy delivery element 14 is inserted into the connector assembly 22.

Gap 482 permits displacement (with or without elastic deformation) in directions 490, 492, and radial expansion 484 of the outer coil 442, within the limits of the recess 456. The outer coil 442 preferably contacts housing 444 (eliminating the gap 482) when a proximal end 36 or 42 is inserted along the axis A.

In addition to radial expansion 484, individual coils 485 on the outer coil 442 can also be radially compressed in direction 488 when engaged with the proximal ends 36, 42 of the therapy delivery element 14 or extension 16. Pre-canted springs generally lack the ability to be radially compressed as disclosed herein. Rather, pre-canted springs are simply canted further in response to such a force. Consequently, the radial compression 488 of the individual coils 485 is an additional degree of freedom for the spring assembly 450 not present in the pre-canted coil springs of the prior art.

The radial play 484 in the contact 400 makes pre-canting the outer coil 442 unnecessary. The present outer coil 442 can be displaced through at least three degrees of freedom to accommodate variations in the contact rings 15 on the proximal end 36, 42 of the therapy delivery element 14 or the extension 16. First, the outer coil 442 can be displaced or shifted linearly in directions 490, 492 within the housing 444. Second, the outer coil 442 can expand radially in direction 484 to the limits of the gap 482. Third, the individual coils 485 of the outer coil 442 can be radially compressed in direction 488.

Figure 5D:
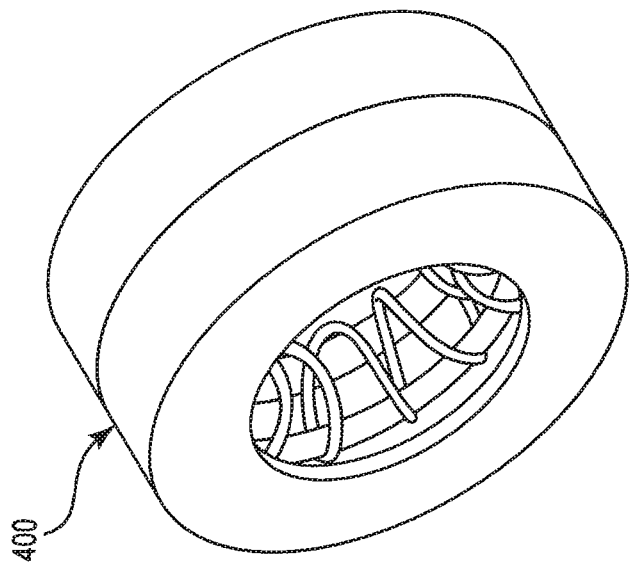
FIG. 5D illustrates the electrical connector of FIG. 5A in a fully assembled configuration.

FIG. 5D illustrates the contact 400 fully assembled. The two portions of the housing 444A, 444B can be joined using a variety of techniques, such as for example, laser welding, adhesives, mechanical interlock, friction fit, and the like.

Figure 6:
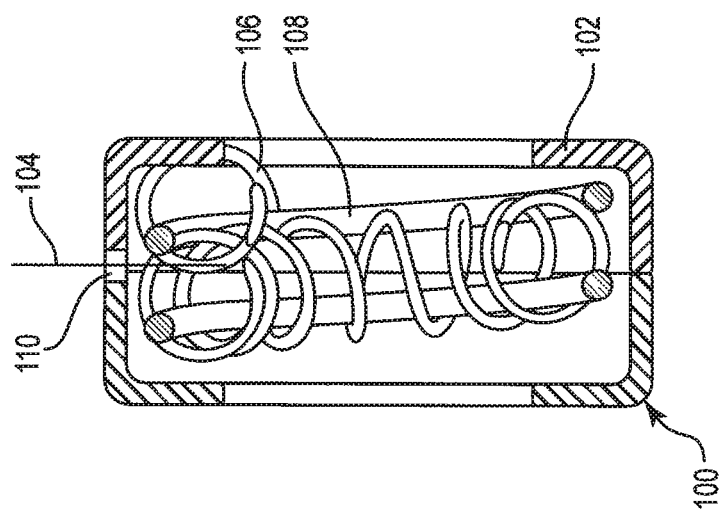
FIG. 6 is a side sectional view of an alternate contact with a pigtail conductor electrically coupled to the coils in accordance with an embodiment of the present disclosure.

FIG. 6 illustrates an alternate contact 100 with a non-conductive housing 102. Electrical conductor 104 is electrically coupled with the coils 106, 108, and extends through opening 110 in the housing 102 to connect with the implantable pulse generator 12. The non-conductive housing 102 permits the contacts 100 to be stacked to form a more compact connector assembly 22.

Figure 7A:
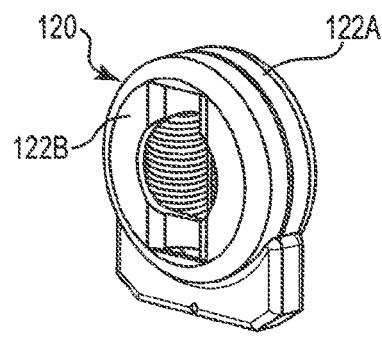
FIG. 7A is a perspective view of an alternate connector in accordance with an embodiment of the present disclosure.
Figure 7B:
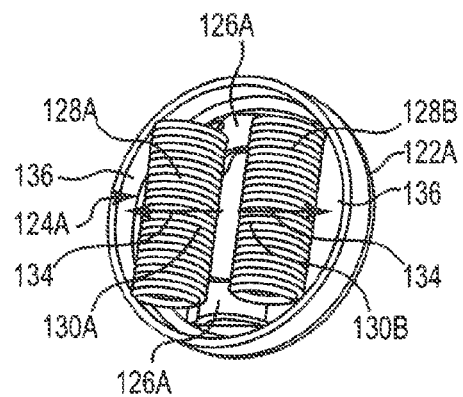
FIG. 7B is a perspective view of the connector of FIG. 7A with the cover removed.
Figure 7C:
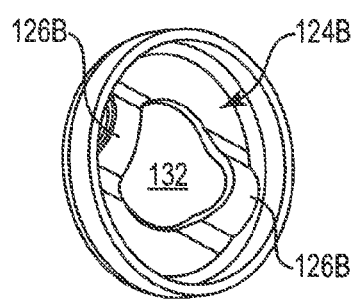
FIG. 7C is a perspective view of the cover for the connector of FIG. 7A.
Figure 7D:
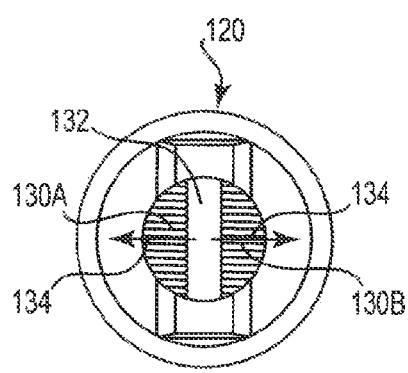
FIG. 7D is a front view of the connector of FIG. 7A.

FIGS. 7A through 7D are various views of an alternate contact 120 in accordance with an embodiment of the present disclosure. As best illustrated in FIGS. 7B and 7C, the two parts of housing 122A, 122B ("122") each include recess 124A, 124B ("124"). Protrusions 126A, 126B ("126") formed in the respective recesses 124 retain coils 128A, 128B ("128") in a desired location.

Center portions 130A, 130B ("130") of the coils 128 extend into center opening 132. As proximal end 36 of therapy delivery element 14 is inserted into the contact 120 center portions 130 of the coils 128 are free to flex radially outward 134 into portions 136 of the recesses 124. The individual coils 128 can also be radially compressed.

Figure 8A:
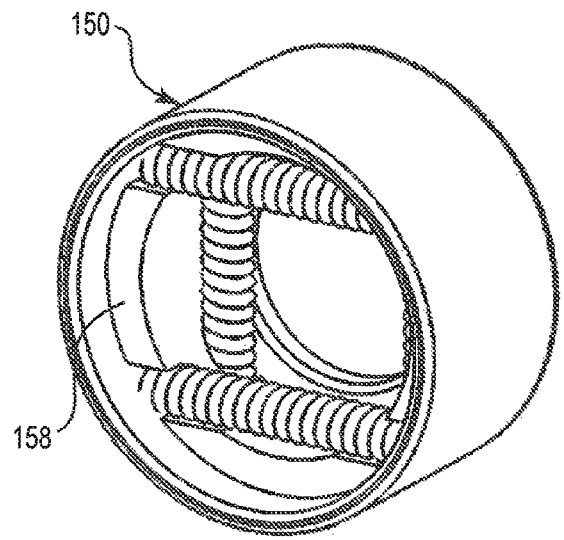
FIG. 8A is a front view of an alternate connector with four linear coils in accordance with an embodiment of the present disclosure.
Figure 8B:
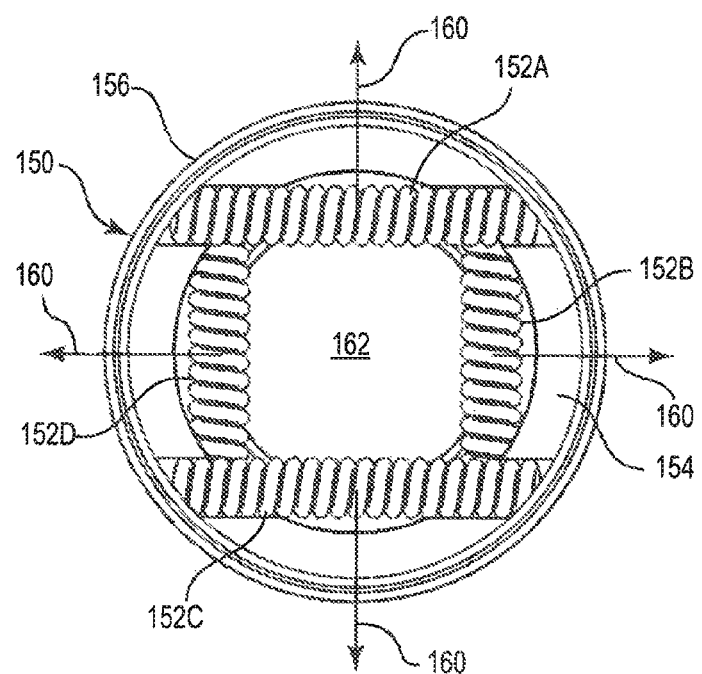
FIG. 8B is a rear view of the connector of FIG. 8A.

FIGS. 8A and 8B illustrate an alternate contact 150 in accordance with an embodiment of the present disclosure. As best illustrated in FIG. 8B, four discrete coils 152A, 152B, 152C, 152D ("152") are positioned in recess 154 of housing 156. The coils 152A, 152C are positioned parallel and adjacent to sidewall 158 of the housing 156. The coils 152B, 152D are also positioned parallel, but behind the coils 152A, 152C. The circular recess 154 permits center portions of the coils 152 to be displaced radially outward 160 away from center opening 162. The individual coils can also be radially compressed or deformed relative to the center opening 162.

In one embodiment, a rear cover is attached to the housing 156 to retain the coils 152 in place. Alternatively, in embodiments where the housing 156 is a non-conductive or dielectric material, a plurality of housings 156 can be stacked together so that the sidewall 158 of one housing acts as the cover for the adjacent contact 150.

Figure 9A:
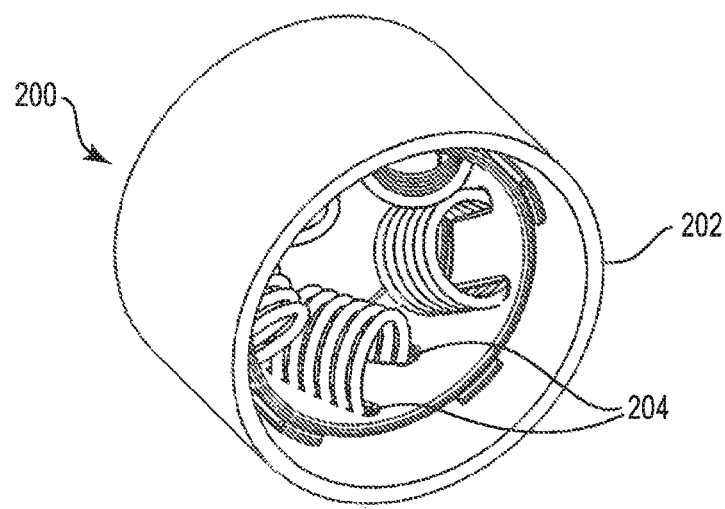
FIGS. 9A through 9C are perspective views of an alternate connector with coils oriented an acute angle relative to the center opening of the contact in accordance with an embodiment of the present disclosure.
Figure 9B:
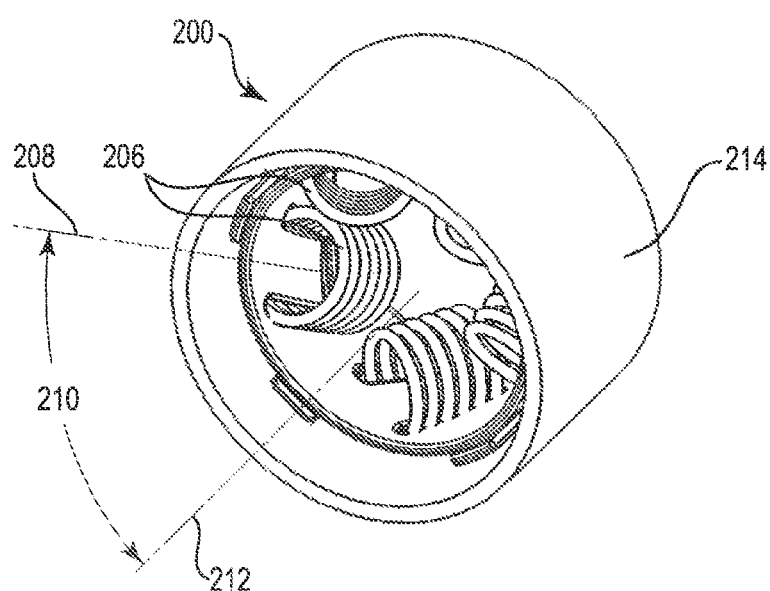
Figure 9C:
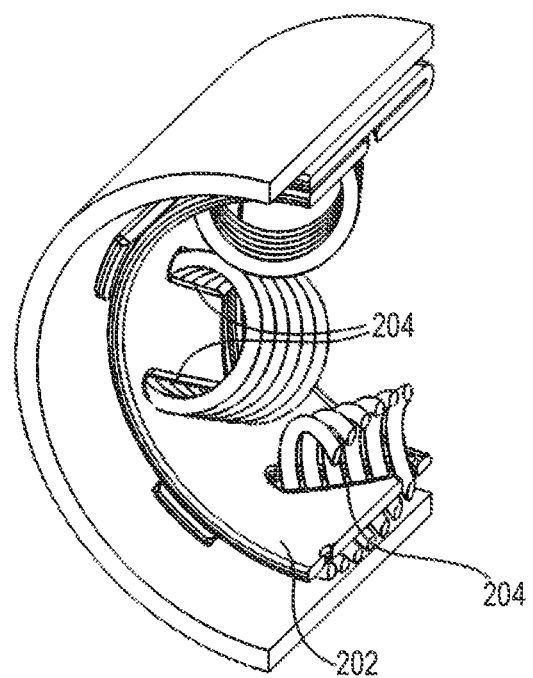

FIGS. 9A through 9C illustrate an alternate contact 200 having insert 202 with a series of slots 204 configured to receive a plurality of coils 206 in accordance with an embodiment of the present disclosure. Center axes 208 of the coils 206 are oriented at an acute angle 210 relative to center axis 212 of the contact 200. Housing 214 retains the coils 206 in the slots 204. In the illustrated embodiment, the individual coils 206 can radially compressed or deformed relative to center axis 212.

Figure 10A:
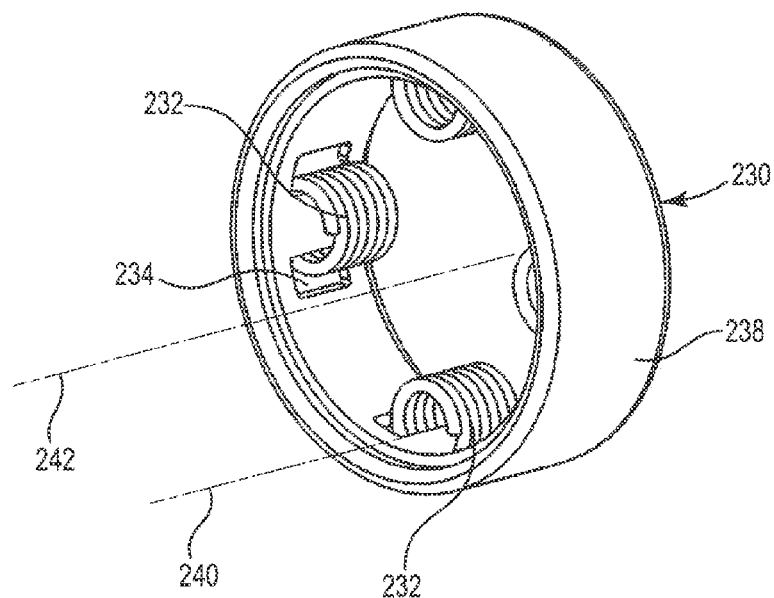
FIGS. 10A and 10B are perspective views of an alternate connector with coils oriented parallel to the center opening of the contact in accordance with an embodiment of the present disclosure.
Figure 10B:
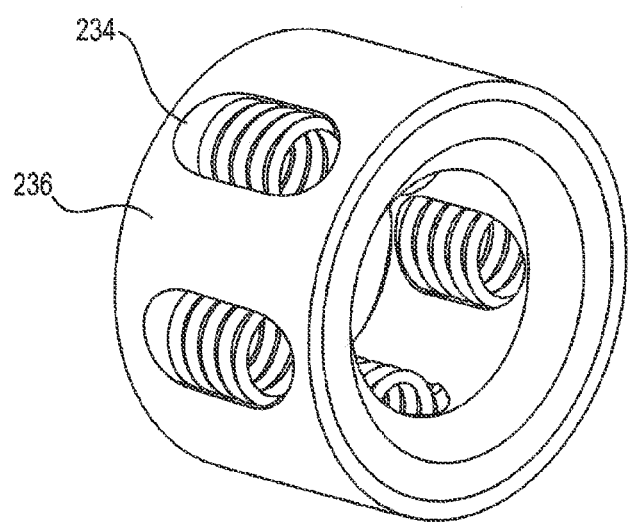

FIGS. 10A and 10B illustrate an alternate contact 230 in accordance with an embodiment of the present disclosure. The coils 232 are again retains in slots 234 formed in insert 236 by housing 238. Center axes 240 of the coils 232 are parallel to center axis 242 of the contact 230. As best illustrated in FIG. 10B, the coils 232 can be displaced radially outward relative to slots 234. The slots 234 are preferably configured to permit the coils 232 to be radially compressed or deformed relative to center axis 242 of the contact 230.

Figure 11A:
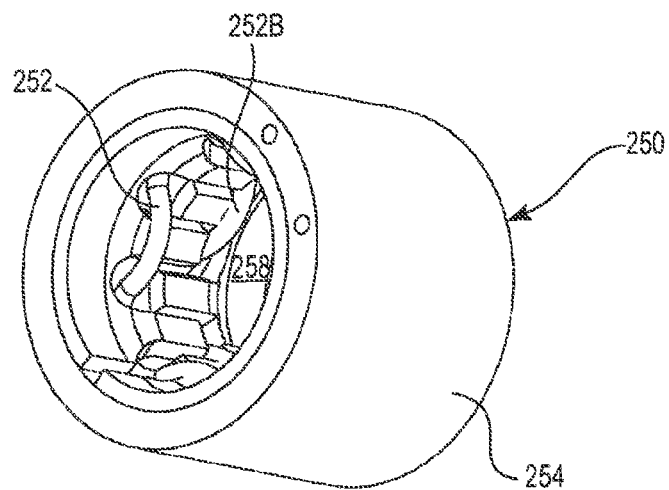
FIGS. 11A through 11C are perspective views of an alternate connector with coils woven on tabs in the housing in accordance with an embodiment of the present disclosure.
Figure 11B:
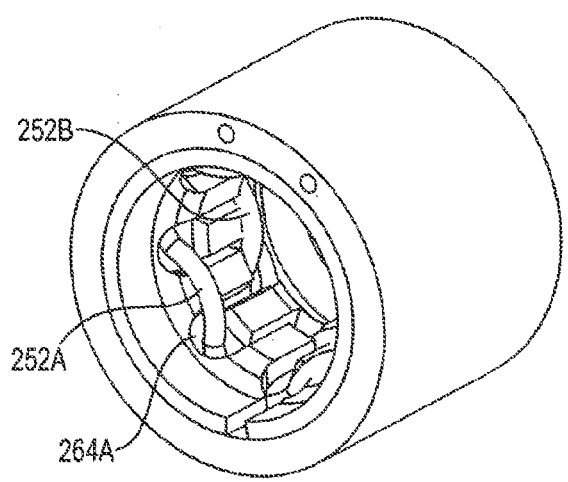
Figure 11C:
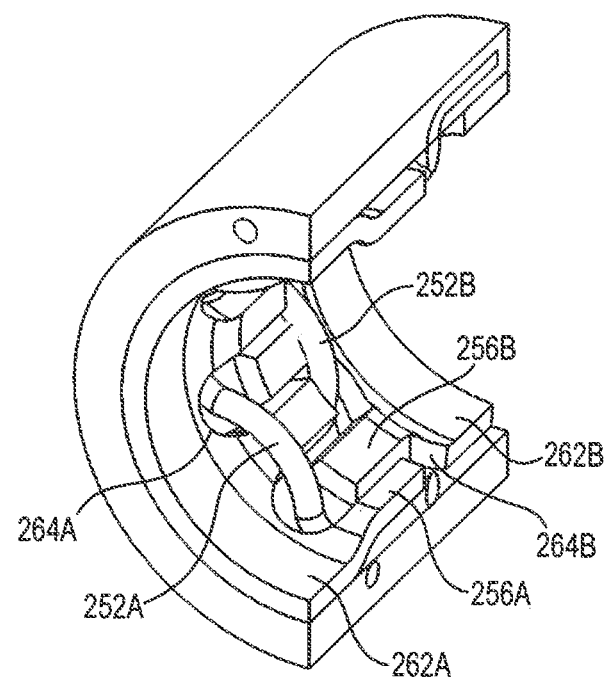

FIGS. 11A and 11B illustrate an alternate contact 250 with woven conductive coils 252A, 252B ("252") in accordance with an embodiment of the present disclosure. Inserts 262A, 262B ("262") include a plurality of interleaving tabs 256A, 256B ("256") that capture coils 252 in spaces 264A, 264B ("264"). The tabs 256 preferably extending generally parallel to center opening 258 of the contact 250. The inserts 262 and the coils 252 are retained in housing 254. The coils 252 can deform radially outward, or compress relative to the housing 254, during insertion of a proximal end of a therapy delivery device or lead extension.

Figure 12:
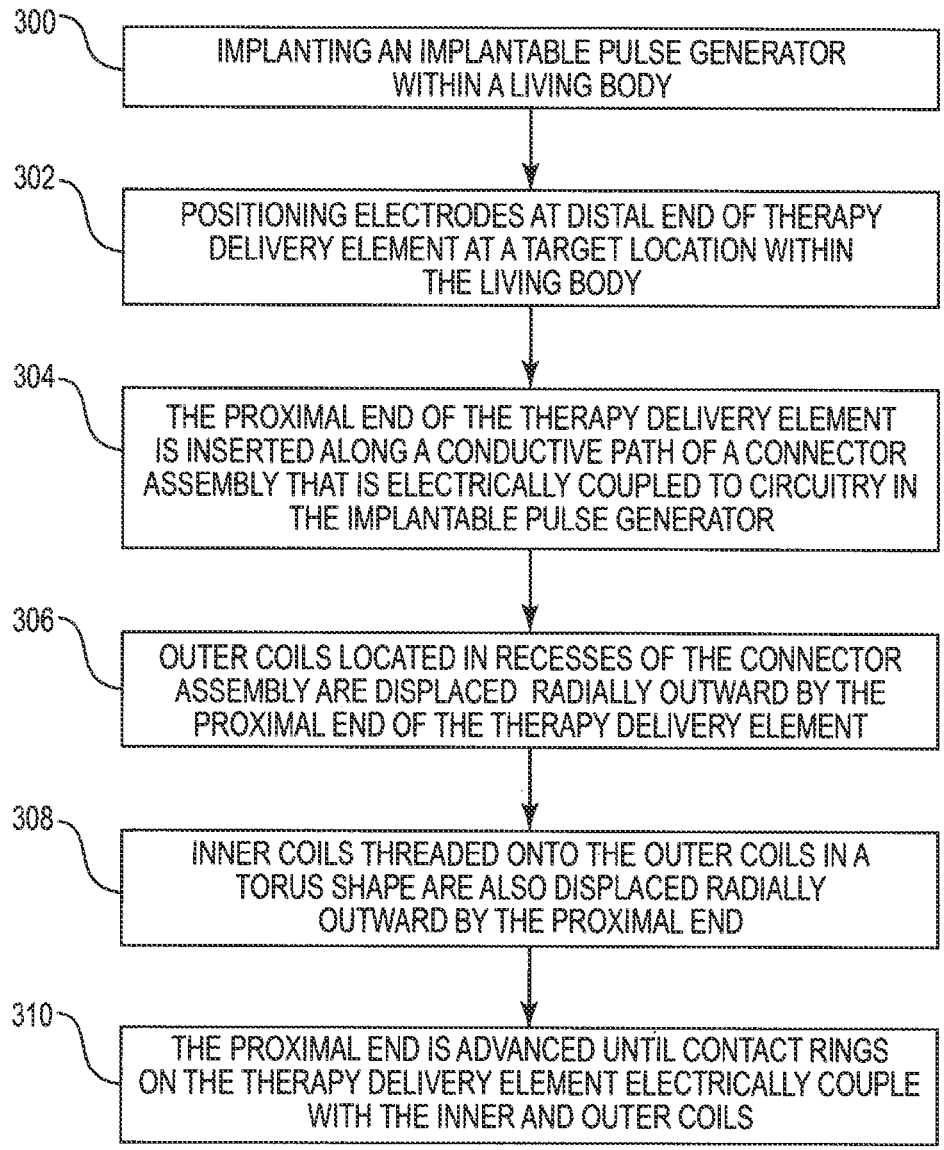
FIG. 12 is a flow diagram of a method of implanting a neurostimulation system within a living body in accordance with an embodiment of the present disclosure.

FIG. 12 is a flow diagram of a method of implanting a neurostimulation system within a living body in accordance with an embodiment of the present disclosure. The method includes the steps of implanting an implantable pulse generator within the living body (300). Electrodes at a distal end of a therapy delivery element are positioned at a target location within the living body (302). The proximal end of the therapy delivery element is inserted along a conductive path of a connector assembly that is electrically coupled to circuitry in the implantable pulse generator (304). Outer coils located in recesses of the connector assembly are displaced radially outward by the proximal end of the therapy delivery element (306). Inner coils threaded onto the outer coils in a toroidal-shape are also displaced radially outward by the proximal end (308). The proximal end is advanced until contact rings on the therapy delivery element electrically couple with the inner and outer coils (310).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. An electrical contact for coupling to a contact ring on an implantable medical device, the electrical contact comprising:
   a housing with a pair of opposing sidewalls, each with center openings oriented generally concentrically around a center axis, the housing including a recess and a first protrusion disposed within the recess to at least partially divide the recess; and
   at least a pair of first coils disposed within the recess and separated from one another by the first protrusion, at least a portion of each of the first coils extending into the center openings, the portion of each of the first coils being configured to flex outwardly with insertion of the contact ring within the electrical contact.

2. The electrical contact of claim 1, wherein, with the first coils flexed outwardly, the first coils are displaced within the recess relative to the center openings.

3. The electrical contact of claim 1, wherein the first protrusion is disposed along a centerline of the housing extending from an interior of at least one of the sidewalls.

4. The electrical contact of claim 3, wherein the first protrusion is disposed on either side of the center opening.

5. The electrical contact of claim 3, wherein the first protrusion extends from the interior of each of the sidewalls.

6. The electrical contact of claim 1, wherein, in an unflexed condition, the first coils are substantially parallel to one another.

7. The electrical contact of claim 1, comprising a pair of second coils disposed within the recess and separated from one another by a second protrusion, at least a portion of each of the second coils extending into the center openings, the portion of each of the second coils being configured to flex outwardly with insertion of the contact ring within the electrical contact.

8. The electrical contact of claim 7, wherein, in an unflexed condition, the second coils are substantially parallel to one another.

9. The electrical contact of claim 7, wherein, in an unflexed condition, the second coils are substantially perpendicular to the first coils.

10. The electrical contact of claim 1, wherein the housing includes a non-conductive material.

11. A connector assembly for coupling to a contact ring on an implantable medical device, the connector assembly comprising:
    a housing with a pair of opposing sidewalls, each with center openings oriented generally concentrically around a center axis, the housing including a recess and a first protrusion disposed within the recess to at least partially divide the recess;
    at least a pair of first coils disposed within the recess and separated from one another by the first protrusion, at least a portion of each of the first coils extending into the center openings, the portion of each of the first coils being configured to flex outwardly with insertion of the contact ring within the electrical contact; and
    a connector assembly housing retaining the electrical contact in a position such that the center openings of the electrical contact are disposed along a conductor path.

12. The connector assembly of claim 11, comprising at least two electrical contacts and a dielectric material separating each of the electrical contacts without blocking the conductor path, wherein the connector assembly housing retains each of the electrical contacts in a position such that the center axes of the electrical contacts are substantially co-linear and the center opening of each of the electrical contacts is disposed along the conductor path, wherein the electrical contacts are positioned to couple to corresponding contact rings of the implantable medical device.

13. The connector assembly of claim 11, wherein, with the first coils flexed outwardly, the first coils are displaced within the recess relative to the center openings.

14. The connector assembly of claim 11, wherein, in an unflexed condition, the first coils are substantially parallel to one another.

15. The connector assembly of claim 11, comprising a pair of second coils disposed within the recess and separated from one another by a second protrusion, at least a portion of each of the second coils extending into the center openings, the portion of each of the second coils being configured to flex outwardly with insertion of the contact ring within the electrical contact.

16. The connector assembly of claim 15, wherein, in an unflexed condition, the second coils are substantially parallel to one another.

17. The connector assembly of claim 15, wherein, in an unflexed condition, the second coils are substantially perpendicular to the first coils.

18. A neurostimulation system comprising:
   an implantable pulse generator including pulse generation circuitry within a pulse generator housing;
   an implantable therapy delivery element including a contact ring on a proximal end of the implantable therapy delivery element; and
   a connector assembly attached to the pulse generator housing, the connector assembly including an electrical contact including:
      a housing with a pair of opposing sidewalls, each with center openings oriented generally concentrically around a center axis, the housing including a recess and a first protrusion disposed within the recess to at least partially divide the recess; and
      at least a pair of first coils disposed within the recess and separated from one another by the first protrusion, at least a portion of each of the first coils extending into the center openings, the portion of each of the first coils being configured to flex outwardly with insertion of the contact ring within the electrical contact, wherein the connector assembly retains the electrical contact in a position such that the center openings of the electrical contact are disposed along a conductor path.

19. The neurostimulation system of claim 18, wherein the connector assembly includes at least two electrical contacts and a dielectric material separating each of the electrical contacts without blocking the conductor path, wherein the connector assembly retains each of the electrical contacts in a position such that the center axes of the electrical contacts are substantially co-linear and the center opening of each of the electrical contacts is disposed along the conductor path, wherein the electrical contacts are positioned to couple to corresponding contact rings of the implantable therapy delivery element.

20. The neurostimulation system of claim 18, comprising a pair of second coils disposed within the recess and separated from one another by a second protrusion, at least a portion of each of the second coils extending into the center openings, the portion of each of the second coils being configured to flex outwardly with insertion of the contact ring within the electrical contact.

* * * * *